United States Patent
Sha et al.

(10) Patent No.: US 7,285,389 B1
(45) Date of Patent: *Oct. 23, 2007

(54) PROTEIN, GENE ENCODING THE SAME, AND METHOD OF UTILIZATION THEREOF

(75) Inventors: Shiken Sha, Kanagawa (JP); Yoshiko Aoki, Kanagawa (JP); Yoshisuke Nishi, Kanagawa (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/937,905

(22) PCT Filed: Mar. 31, 2000

(86) PCT No.: PCT/JP00/02080

§ 371 (c)(1),
(2), (4) Date: Oct. 1, 2001

(87) PCT Pub. No.: WO00/60075

PCT Pub. Date: Oct. 12, 2000

(30) Foreign Application Priority Data

Apr. 1, 1999 (JP) .................................. 11/095092

(51) Int. Cl.
*G01N 33/50* (2006.01)
*C12N 15/12* (2006.01)
*C12N 15/63* (2006.01)
*C12N 5/10* (2006.01)
*C07K 14/705* (2006.01)

(52) U.S. Cl. ........................ 435/7.1; 435/7.2; 435/7.21; 435/325; 435/252.3; 435/254.11; 435/320.1; 435/69.1; 536/23.1; 536/23.5; 530/350

(58) Field of Classification Search ............... 536/23.1, 536/23.5; 530/350; 514/2, 12; 435/7.1, 435/320.1, 325, 252.3, 254.11
See application file for complete search history.

(56) References Cited

FOREIGN PATENT DOCUMENTS

| EP | A2-892050 | 1/1999 |
|----|-----------|--------|
| JP | A11-106400 | 4/1999 |

OTHER PUBLICATIONS

Wells, 1990, Biochemistry 29:8509-8517.*
Ngo et al., 1994, The Protein Folding Problem and Tertiary Structure Prediction, Merz et al., eds., Birkhauser, Boston, pp. 492-495.*
McGuiness et al. (1991, The Lancet 337:514-7).*
Daniel et al. (1994), Virology 202:540-9).*
Nishi et al., Proceeding of Biotechnology Symposium, vol. 15, pp. 159-164 (1997).
Aoki et al., Cytokine, vol. 10, No. 8, pp. 596-602 (1998).
Nishi et al., Proceedings of Biotechnology Symposium, vol. 16, pp. 161-166 (1998).
Database Publication No XP002195347 of SHA et al., "A cDNA sequence from murine monocyte macrophage" Jun. 18, 1999.
Database Publication No. XP001068354 of Aoki et al., In Vitro Cellular & Developmental Biology Animal, vol. 36, No. 3 part 2 (2000) p. 75.

* cited by examiner

*Primary Examiner*—Elizabeth C. Kemmerer
(74) *Attorney, Agent, or Firm*—Birch, Stewart, Kolasch & Birch, LLP

(57) ABSTRACT

The present invention provides, as a gene encoding an antigen recognized by G-CSF-inducing antibodies, a gene encoding:

(a) a protein having the amino acid sequence listed as SEQ ID NO:2 of the Sequence Listing;
(b) a protein having the amino acid sequence listed as SEQ ID NO:2 of the Sequence Listing with one or more amino acid deletions, substitutions, additions or insertions and also binding to an antibody or its fragment that is active to induce granulocyte colony-stimulating factor; or
(c) a protein having at least 50% homology with the amino acid sequence listed as SEQ ID NO:2 and also binding to an antibody or its fragment that is active to induce granulocyte colony-stimulating factor.

14 Claims, No Drawings

SEQUENCE LISTING

```
<160> NUMBER OF SEQ ID NOS: 8

<210> SEQ ID NO 1
<211> LENGTH: 840
<212> TYPE: DNA
<213> ORGANISM: Mus sp.
<220> FEATURE:
<221> NAME/KEY: CDS
<222> LOCATION: (6)..(731)
<223> OTHER INFORMATION:
<220> FEATURE:
<221> NAME/KEY: misc_feature
<222> LOCATION: (1)..(840)
<223> OTHER INFORMATION: Mouse macrophage cell RAW 264.7

<400> SEQUENCE: 1 gaacc atg tct ggc tgt caa gct caa gga gac tgt tgc tcg cgg ccg tgt     50
      Met Ser Gly Cys Gln Ala Gln Gly Asp Cys Cys Ser Arg Pro Cys
      1               5                  10                  15 ggc gcg cag gac aag gag cac ccc cga ttc ctg atc cca gaa ctt tgc       98
Gly Ala Gln Asp Lys Glu His Pro Arg Phe Leu Ile Pro Glu Leu Cys
                20                  25                  30 aaa cag ttt tac cat ctg ggc tgg gtc act ggc act gga ggg gga atc      146
Lys Gln Phe Tyr His Leu Gly Trp Val Thr Gly Thr Gly Gly Gly Ile
            35                  40                  45 agc ttg aag cat ggc aat gaa atc tac att gct ccc tca ggc gtg caa      194
Ser Leu Lys His Gly Asn Glu Ile Tyr Ile Ala Pro Ser Gly Val Gln
        50                  55                  60 aag gag cgc att cag cca gaa gac atg ttt gtg tgt gac att aat gag      242
Lys Glu Arg Ile Gln Pro Glu Asp Met Phe Val Cys Asp Ile Asn Glu
    65                  70                  75 cag gac ata agc ggg cct cca gca tct aag aag ctg aaa aaa agc cag      290
Gln Asp Ile Ser Gly Pro Pro Ala Ser Lys Lys Leu Lys Lys Ser Gln
```

```
               80                  85                  90                  95
tgc act cct ctt ttc atg aat gct tat acc atg aga gga gct ggc gca           338
Cys Thr Pro Leu Phe Met Asn Ala Tyr Thr Met Arg Gly Ala Gly Ala
                100                 105                 110 gtg att cat acc cac tct aaa gct gct gtg atg gct acc ctt ctg ttt           386
Val Ile His Thr His Ser Lys Ala Ala Val Met Ala Thr Leu Leu Phe
            115                 120                 125 cca gga cag gag ttt aaa att aca cat caa gag atg atc aaa gga ata           434
Pro Gly Gln Glu Phe Lys Ile Thr His Gln Glu Met Ile Lys Gly Ile
        130                 135                 140 agg aaa tgt acc tca gga ggc tat tac aga tac gat gat atg tta gtg           482
Arg Lys Cys Thr Ser Gly Gly Tyr Tyr Arg Tyr Asp Asp Met Leu Val
    145                 150                 155 gta cct att att gag aac act cct gaa gag aag gat ctc aaa gaa agg           530
Val Pro Ile Ile Glu Asn Thr Pro Glu Glu Lys Asp Leu Lys Glu Arg
160                 165                 170                 175 atg gct cat gcc atg aat gag tac cca gac tcc tgt gcg gtt ctt gtc           578
Met Ala His Ala Met Asn Glu Tyr Pro Asp Ser Cys Ala Val Leu Val
                180                 185                 190 cgg cgt cat ggg gtg tac gtg tgg gga gaa aca tgg gag aaa gca aaa           626
Arg Arg His Gly Val Tyr Val Trp Gly Glu Thr Trp Glu Lys Ala Lys
            195                 200                 205 acc atg tgt gag tgt tat gac tac ctg ttt gac att gct gtc tcc atg           674
Thr Met Cys Glu Cys Tyr Asp Tyr Leu Phe Asp Ile Ala Val Ser Met
        210                 215                 220 aag aag atg gga ctc gat cca aca cag ctc cca gtt gga gaa aat gga           722
Lys Lys Met Gly Leu Asp Pro Thr Gln Leu Pro Val Gly Glu Asn Gly
    225                 230                 235 att gtg taa gccaagtgga tgcctaagca tctccaacaa taaaacaaac                   771
Ile Val
240 tcaattatgc cttaaataaa actcagctgc ttttaaaaaa aaaaaaaaaa aaaaaaaaaa         831 aaaaaaaaa                                                                 840

<210> SEQ ID NO 2
<211> LENGTH: 241
<212> TYPE: PRT
<213> ORGANISM: Mus sp.
<220> FEATURE:
<221> NAME/KEY: misc_feature
<222> LOCATION: (1)..(241)
<223> OTHER INFORMATION: Mouse macrophage cell RAW 264.7

<400> SEQUENCE: 2

Met Ser Gly Cys Gln Ala Gln Gly Asp Cys Cys Ser Arg Pro Cys Gly
1               5                   10                  15

Ala Gln Asp Lys Glu His Pro Arg Phe Leu Ile Pro Glu Leu Cys Lys
            20                  25                  30

Gln Phe Tyr His Leu Gly Trp Val Thr Gly Thr Gly Gly Ile Ser
        35                  40                  45

Leu Lys His Gly Asn Glu Ile Tyr Ile Ala Pro Ser Gly Val Gln Lys
    50                  55                  60

Glu Arg Ile Gln Pro Glu Asp Met Phe Val Cys Asp Ile Asn Glu Gln
65                  70                  75                  80

Asp Ile Ser Gly Pro Pro Ala Ser Lys Lys Leu Lys Lys Ser Gln Cys
                85                  90                  95

Thr Pro Leu Phe Met Asn Ala Tyr Thr Met Arg Gly Ala Gly Ala Val
            100                 105                 110
```

-continued

```
Ile His Thr His Ser Lys Ala Ala Val Met Ala Thr Leu Leu Phe Pro
        115                 120                 125

Gly Gln Glu Phe Lys Ile Thr His Gln Glu Met Ile Lys Gly Ile Arg
130                 135                 140

Lys Cys Thr Ser Gly Gly Tyr Tyr Arg Tyr Asp Asp Met Leu Val Val
145                 150                 155                 160

Pro Ile Ile Glu Asn Thr Pro Glu Lys Asp Leu Lys Glu Arg Met
                165                 170                 175

Ala His Ala Met Asn Glu Tyr Pro Asp Ser Cys Ala Val Leu Val Arg
                180                 185                 190

Arg His Gly Val Tyr Val Trp Gly Glu Thr Trp Glu Lys Ala Lys Thr
            195                 200                 205

Met Cys Glu Cys Tyr Asp Tyr Leu Phe Asp Ile Ala Val Ser Met Lys
    210                 215                 220

Lys Met Gly Leu Asp Pro Thr Gln Leu Pro Val Gly Glu Asn Gly Ile
225                 230                 235                 240

Val
```

<210> SEQ ID NO 3
<211> LENGTH: 924
<212> TYPE: DNA
<213> ORGANISM: Homo sapiens
<220> FEATURE:
<221> NAME/KEY: CDS
<222> LOCATION: (46)..(774)
<223> OTHER INFORMATION:
<220> FEATURE:
<221> NAME/KEY: misc_feature
<222> LOCATION: (1)..(924)
<223> OTHER INFORMATION: Human normal brain tissue

<400> SEQUENCE: 3

```
aagccgtgcg gagattggag gccgcgcggg tccctggtct gggcc atg tct ggc tgt       57
                                                 Met Ser Gly Cys
                                                  1 gat gct tgg gag gga gac tgt tgt tcc cgg aga tgc ggc gcg cag gac       105
Asp Ala Trp Glu Gly Asp Cys Cys Ser Arg Arg Cys Gly Ala Gln Asp
 5                  10                  15                  20 aag gag cat cca aga tac ctg atc cca gaa ctt tgc aaa cag ttt tac       153
Lys Glu His Pro Arg Tyr Leu Ile Pro Glu Leu Cys Lys Gln Phe Tyr
                 25                  30                  35 cat tta ggc tgg gtc act ggg act gga gga gga att agc ttg aag cat       201
His Leu Gly Trp Val Thr Gly Thr Gly Gly Gly Ile Ser Leu Lys His
             40                  45                  50 ggc gat gaa atc tac att gct cct tca gga gtg caa aag gaa cga att       249
Gly Asp Glu Ile Tyr Ile Ala Pro Ser Gly Val Gln Lys Glu Arg Ile
         55                  60                  65 cag cct gaa gac atg ttt gtt tat gat ata aat gaa aag gac ata agt       297
Gln Pro Glu Asp Met Phe Val Tyr Asp Ile Asn Glu Lys Asp Ile Ser
 70                  75                  80 gga cct tcg cca tcg aag aag cta aaa aaa agc cag tgt act cct ctt       345
Gly Pro Ser Pro Ser Lys Lys Leu Lys Lys Ser Gln Cys Thr Pro Leu
85                  90                  95                 100 ttc atg aat gct tac aca atg aga gga gca ggt gca gtg att cat acc       393
Phe Met Asn Ala Tyr Thr Met Arg Gly Ala Gly Ala Val Ile His Thr
                105                 110                 115 cac tct aaa gct gct gtg atg gcc acc ctt ctc ttt cca gga cgg gag       441
His Ser Lys Ala Ala Val Met Ala Thr Leu Leu Phe Pro Gly Arg Glu
            120                 125                 130 ttt aaa att aca cat caa gag atg ata aaa gga ata aag aaa tgt act       489
```

```
                                                      -continued

Phe Lys Ile Thr His Gln Glu Met Ile Lys Gly Ile Lys Lys Cys Thr
        135                 140                 145 tcc gga ggg tat tat aga tat gat gat atg tta gtg gta ccc att att        537
Ser Gly Gly Tyr Tyr Arg Tyr Asp Asp Met Leu Val Val Pro Ile Ile
150                 155                 160 gag aat aca cct gag gag aaa gac ctc aaa gat aga atg gct cat gca        585
Glu Asn Thr Pro Glu Glu Lys Asp Leu Lys Asp Arg Met Ala His Ala
165                 170                 175                 180 atg aat gaa tac cca gac tcc tgt gca gta ctg gtc aga cgt cat gga        633
Met Asn Glu Tyr Pro Asp Ser Cys Ala Val Leu Val Arg Arg His Gly
                185                 190                 195 gta tat gtg tgg ggg gaa aca tgg gag aag gcc aaa acc atg tgt gag        681
Val Tyr Val Trp Gly Glu Thr Trp Glu Lys Ala Lys Thr Met Cys Glu
            200                 205                 210 tgt tat gac tat tta ttt gat att gcc gta tca atg aag aaa gta gga        729
Cys Tyr Asp Tyr Leu Phe Asp Ile Ala Val Ser Met Lys Lys Val Gly
        215                 220                 225 ctt gat cct tca cag ctc cca gtt gga gaa aat gga att gtc taa            774
Leu Asp Pro Ser Gln Leu Pro Val Gly Glu Asn Gly Ile Val
    230                 235                 240 gccaaagaa agtctaatta tatacagaga taaagctaaa cgtaattatt atttaaatga       834
aagctatttt tttaaatgaa ttgaaatttt tcatgatgct actaatttgc cactaaatac     894
tgcaaatggt caccctgaat ctcttctgac                                      924

<210> SEQ ID NO 4
<211> LENGTH: 242
<212> TYPE: PRT
<213> ORGANISM: Homo sapiens
<220> FEATURE:
<221> NAME/KEY: misc_feature
<222> LOCATION: (1)..(242)
<223> OTHER INFORMATION: Human normal brain tissue

<400> SEQUENCE: 4

Met Ser Gly Cys Asp Ala Trp Glu Gly Asp Cys Cys Ser Arg Arg Cys
1               5                   10                  15

Gly Ala Gln Asp Lys Glu His Pro Arg Tyr Leu Ile Pro Glu Leu Cys
            20                  25                  30

Lys Gln Phe Tyr His Leu Gly Trp Val Thr Gly Thr Gly Gly Ile
        35                  40                  45

Ser Leu Lys His Gly Asp Glu Ile Tyr Ile Ala Pro Ser Gly Val Gln
    50                  55                  60

Lys Glu Arg Ile Gln Pro Glu Asp Met Phe Val Tyr Asp Ile Asn Glu
65                  70                  75                  80

Lys Asp Ile Ser Gly Pro Ser Pro Ser Lys Leu Lys Lys Ser Gln
                85                  90                  95

Cys Thr Pro Leu Phe Met Asn Ala Tyr Thr Met Arg Gly Ala Gly Ala
            100                 105                 110

Val Ile His Thr His Ser Lys Ala Ala Val Met Ala Thr Leu Leu Phe
        115                 120                 125

Pro Gly Arg Glu Phe Lys Ile Thr His Gln Glu Met Ile Lys Gly Ile
    130                 135                 140

Lys Lys Cys Thr Ser Gly Gly Tyr Tyr Arg Tyr Asp Asp Met Leu Val
145                 150                 155                 160

Val Pro Ile Ile Glu Asn Thr Pro Glu Glu Lys Asp Leu Lys Asp Arg
                165                 170                 175

Met Ala His Ala Met Asn Glu Tyr Pro Asp Ser Cys Ala Val Leu Val
```

```
                    180                 185                 190
Arg Arg His Gly Val Tyr Val Trp Gly Glu Thr Trp Glu Lys Ala Lys
        195                 200                 205

Thr Met Cys Glu Cys Tyr Asp Tyr Leu Phe Asp Ile Ala Val Ser Met
    210                 215                 220

Lys Lys Val Gly Leu Asp Pro Ser Gln Leu Pro Val Gly Glu Asn Gly
225                 230                 235                 240

Ile Val

<210> SEQ ID NO 5
<211> LENGTH: 19
<212> TYPE: DNA
<213> ORGANISM: Artificial Sequence
<220> FEATURE:
<223> OTHER INFORMATION: Sense primer of position 4 to 22 of the mouse
      antigen gene MMR19

<400> SEQUENCE: 5
ccatgtctgg ctgtcaagc                                              19

<210> SEQ ID NO 6
<211> LENGTH: 21
<212> TYPE: DNA
<213> ORGANISM: Artificial Sequence
<220> FEATURE:
<223> OTHER INFORMATION: An antisense primer of position 714 to 724 of
      the mouse antigen gene MMR19

<400> SEQUENCE: 6
ccattttctc caactgggag c                                           21

<210> SEQ ID NO 7
<211> LENGTH: 23
<212> TYPE: DNA
<213> ORGANISM: Artificial Sequence
<220> FEATURE:
<223> OTHER INFORMATION: Antisense primer of the 3' RACE fragment

<400> SEQUENCE: 7
gtcagaagag attcagggtg acc                                         23

<210> SEQ ID NO 8
<211> LENGTH: 21
<212> TYPE: DNA
<213> ORGANISM: Artificial Sequence
<220> FEATURE:
<223> OTHER INFORMATION: Sense primer of the 5' RACE fragment

<400> SEQUENCE: 8
aagccgtgcg gagattggag g                                           21
```

PROTEIN, GENE ENCODING THE SAME, AND METHOD OF UTILIZATION THEREOF

This application is the national phase under 35 U.S.C. § 371 of PCT International Application No. PCT/JP00/02080 which has an International filing date of Mar. 31, 2000, which designated the United States of America.

TECHNICAL FIELD

The present invention relates to a protein which is reactive with antibodies that are active to induce granulocyte colony-stimulating factor, to a gene encoding it and to a method for their use.

BACKGROUND ART

Granulocyte colony-stimulating factor (G-CSF) has a molecular weight of approximately 18,000 to 22,000 and consists of 174 (in rare cases 178) amino acids in the case of humans and 178 amino acids in the case of mice. It is a glycoprotein that induces differentiation and proliferation of neutrophils, one of the types of leukocytes.

G-CSF has a potential of survival-extension and functional promotion to the mature neutrophils, and also has ability to form erythroblasts in response to erythropoietin and blast cell colonies in response to interleukin-3. Cells that produce G-CSF are macrophages, stroma cells, monocytes, T lymphocytes, fibroblasts, vascular endothelial cells and so forth.

Administration of G-CSF drug exhibits a therapeutic effect on neutropenia induced by side effect of anticancer agents, or neutropenia following bone marrow transplantation, and a therapeutic effect on anaplastic anemia. Because of its low stability in the blood, however, it requires frequent administration, and because its administration is limited to the intravenous route, this has resulted in a great deal of pain and burden to the patient and physician. Furthermore, administration of G-CSF as a drug has been reported to cause ostalgia as a side-effect. The alternative option of direct administration of macrophages or stroma cells that produce G-CSF will produce the risk of unknown side-effects since the cells contain numerous proteins and other substances, and therefore such treatment has not been practiced.

Because administration of G-CSF itself for differentiation and proliferation of neutrophils provoke ostalgia as a side-effect, and it also requires frequent administration and increases the pain and burden to the patient and physician, it has been strongly desired to develop an alternative treatment method; however, no such method has yet been established.

With the intent of causing production of G-CSF and differentiation and proliferation of neutrophils without administration of G-CSF itself, the present inventors have already succeeded in providing G-CSF inducing antibodies (Japanese Patent Application HEI No. 9-266591 (Sep. 30, 1997), Japanese Unexamined Patent Publication HEI No. 11-106400 (Apr. 20, 1999)).

However, the antigens recognized by the G-CSF inducing antibodies have not yet been discovered.

One problem to be solved by the present invention, therefore, is to identify an antigen recognized by G-CSF inducing antibodies. Another problem to be solved by the invention is to clone and identify the gene encoding the antigen recognized by the G-CSF inducing antibodies.

DISCLOSURE OF THE INVENTION

As a result of diligent research aimed at solving the problems described above, the present inventors used monoclonal antibodies with G-CSF inducing ability as probes for immunoscreening of a cDNA library derived from macrophage cells, and as a result succeeded in isolating 3 positive clones, and then further determined the nucleotide sequences thereof, to thus arrive at the present invention. The present inventors also determined the nucleotide sequence of the human antigen gene.

In other words, the present invention provides a gene encoding: (a) a protein having the amino acid sequence listed as SEQ ID NO:2 of the Sequence Listing; (b) a protein having the amino acid sequence listed as SEQ ID NO:2 of the Sequence Listing with one or more amino acid deletions, substitutions, additions or insertions and also binding to an antibody or its fragment that is active to induce granulocyte colony-stimulating factor; or (c) a protein having at least 50% homology with the amino acid sequence listed as SEQ ID NO:2 and also binding to an antibody or its fragment that is active to induce granulocyte colony-stimulating factor.

The invention further provides a gene encoding: (a) a protein having the amino acid sequence listed as SEQ ID NO:4 of the Sequence Listing; (b) a protein having the amino acid sequence listed as SEQ ID NO:4 of the Sequence Listing with one or more amino acid deletions, substitutions, additions or insertions and also binding to an antibody or its fragment that is active to induce granulocyte colony-stimulating factor; or (c) a protein having at least 50% homology with the amino acid sequence listed as SEQ ID NO:4 and also binding to an antibody or its fragment that is active to induce granulocyte colony-stimulating factor.

The invention further provides a gene having: (a) the nucleotide sequence listed as SEQ ID NO:1 of the Sequence Listing; (b) a nucleotide sequence which is the nucleotide sequence listed as SEQ ID NO:1 of the Sequence Listing with one or more nucleotide deletions, substitutions, additions or insertions and which encodes a protein that can bind to an antibody or its fragment that is active to induce granulocyte colony-stimulating factor; or (c) a nucleotide sequence which hybridizes with DNA having the nucleotide sequence listed as SEQ ID NO:1 of the Sequence Listing under stringent conditions and encodes a protein that can bind to an antibody or its fragments that are active to induce granulocyte colony-stimulating factor.

The invention further provides a gene having: (a) the nucleotide sequence listed as SEQ ID NO:3 of the Sequence Listing; (b) a nucleotide sequence which is the nucleotide sequence listed as SEQ ID NO:3 of the Sequence Listing with one or more nucleotide deletions, substitutions, additions or insertions and which encodes a protein that can bind to an antibody or its fragment that is active to induce granulocyte colony-stimulating factor; or (c) a nucleotide sequence which hybridizes with DNA having the nucleotide sequence listed as SEQ ID NO:3 of the Sequence Listing under stringent conditions and encodes a protein that can bind to an antibody or its fragment that is active to induce granulocyte colony-stimulating factor.

The antibody that is active to induce granulocyte colony-stimulating factor mentioned above is, for example, the monoclonal antibody produced by a hybridoma of the cell line deposited as FERM BP-6103.

According to the invention, the gene is a gene derived from a mouse or human.

The invention further provides a DNA fragment containing: (1) the nucleotide sequence from position 519 to position 736, the nucleotide sequence from position 666 to position 689, the nucleotide sequence from position 381 to position 403 or the nucleotide sequence from position 709 to position 727 of the nucleotide sequence listed as SEQ ID NO:1 of the Sequence Listing; (2) a nucleotide sequence which is any of the nucleotide sequences of (1) above with one or more nucleotide deletions, substitutions, additions or insertions; or (3) a nucleotide sequence which has at least 80% homology with any of the nucleotide sequences of (1) above.

The invention further provides a gene containing: (1) the nucleotide sequence from position 519 to position 736, the nucleotide sequence from position 666 to position 689, the nucleotide sequence from position 381 to position 403 or the nucleotide sequence from position 709 to position 727 of the nucleotide sequence listed as SEQ ID NO:1 of the Sequence Listing; (2) a nucleotide sequence which is any of the nucleotide sequences of (1) above with one or more nucleotide deletions, substitutions, additions or insertions; or (3) a nucleotide sequence which has at least 80% homology with any of the nucleotide sequences of (1) above; and encoding a protein that can bind to an antibody or its fragments that are active to induce granulocyte colony-stimulating factor.

The invention further provides any of the following proteins: (a) a protein having the amino acid sequence listed as SEQ ID NO:2 of the Sequence Listing; (b) a protein having the amino acid sequence listed as SEQ ID NO:2 of the Sequence Listing with one or more amino acid deletions, substitutions, additions or insertions and also binding to an antibody or its fragment that is active to induce granulocyte colony-stimulating factor; (c) a protein having at least 50% homology with the amino acid sequence listed as SEQ ID NO:2 and also binding to an antibody or its fragment that is active to induce granulocyte colony-stimulating factor; or (d) a protein that is encoded by DNA which hybridizes with DNA having the nucleotide sequence listed as SEQ ID NO:1 of the Sequence Listing under stringent conditions and that binds to an antibody or its fragments that are active to induce granulocyte colony-stimulating factor.

The invention further provides any of the following proteins: (a) a protein having the amino acid sequence listed as SEQ ID NO:4 of the Sequence Listing; (b) a protein having the amino acid sequence listed as SEQ ID NO:4 of the Sequence Listing with one or more amino acid deletions, substitutions, additions or insertions and also binding to an antibody or its fragment that is active to induce granulocyte colony-stimulating factor; (c) a protein having at least 50% homology with the amino acid sequence listed as SEQ ID NO:4 and also binding to an antibody or its fragment that is active to induce granulocyte colony-stimulating factor; or (d) a protein that is encoded by DNA which hybridizes with DNA having the nucleotide sequence listed as SEQ ID NO:3 of the Sequence Listing under stringent conditions and that binds to an antibody or its fragment that is active to induce granulocyte colony-stimulating factor.

The antibody that is active to induce granulocyte colony-stimulating factor mentioned above is, for example, the monoclonal antibody produced by a hybridoma of the cell line deposited as FERM BP-6103.

According to the invention, the protein is preferably a protein derived from mammals and most preferably from a mouse or human.

The invention further provides a protein comprising any of the followings: (1) the amino acid sequence from residues 1 to 91, the amino acid sequence from residues 50 to 146, the amino acid sequence from residues 1 to 78, the amino acid sequence from residues 200 to 241, the amino acid sequence from residues 172 to 241, the amino acid sequence from residues 103 to 150 or the amino acid sequence from residues 169 to 241 of the amino acid sequence listed as SEQ ID NO:2 of the Sequence Listing; (2) an amino acid sequence which is any of the amino acid sequences of (1) above with one or more amino acid deletions, substitutions, additions or insertions; or (3) an amino acid sequence having at least 70% homology with any of the amino acid sequences of (1) above.

The invention further provides a protein comprising any of the followings: (1) the amino acid sequence from residues 1 to 91, the amino acid sequence from residues 50 to 146, the amino acid sequence from residues 1 to 78, the amino acid sequence from residues 200 to 241, the amino acid sequence from residues 172 to 241, the amino acid sequence from residues 103 to 150 or the amino acid sequence from residues 169 to 241 of the amino acid sequence listed as SEQ ID NO:2 of the Sequence Listing; (2) an amino acid sequence which is any of the amino acid sequences of (1) above with one or more amino acid deletions, substitutions, additions or insertions; or (3) an amino acid sequence having at least 70% homology with any of the amino acid sequences of (1) above, and also binding to an antibody or its fragments that are active to induce granulocyte colony-stimulating factor.

The invention further provides an antibody or fragment thereof, for the aforementioned protein of the invention. The antibody is preferably a monoclonal antibody, and most preferably a human-type monoclonal antibody or human monoclonal antibody.

The invention further provides a recombinant vector containing a gene or a DNA fragment according to the invention.

The invention further provides a transformant comprising a recombinant vector containing a gene or a DNA fragment according to the invention.

The invention further provides a receptor for a substance that can induce production of granulocyte colony-stimulating factor, comprising a protein according to the invention.

The invention further provides a method employing a protein of the invention for screening of a useful substance (for example, an agonist or antagonist for the protein), the substance obtained by the screening method and a useful substance that can bind to a receptor (for example, an agonist or antagonist for the receptor).

The invention further provides a pharmaceutical compounds comprising a gene, a DNA fragment, a protein (or a protein fragment), an antibody (or an antibody fragment), a receptor or a substance according to the invention (particularly a pharmaceutical compounds for diagnosis, prevention or treatment of infectious diseases or neutropenia), and a treatment method employing it.

DETAILED DESCRIPTION OF THE INVENTION

Embodiments and working methods of the invention will now be explained in detail.

Prior to the present invention, the present inventors succeeded in obtaining antibodies by direct immunization of macrophages and isolating G-CSF inducing antibodies among the obtained antibodies (Japanese Patent Application HEI No. 9-266591, all of the content of which is incorporated in the present specification by reference). The gene of the present invention was isolated by using these antibodies as a probe for screening of a cDNA library derived from mouse macrophages, and the protein encoded by the gene of the invention is characterized by the ability to bind to the antibodies or the fragments thereof which have granulocyte colony-stimulating factor-inducing activity.

(Antibodies or Fragments Thereof which have Granulocyte Colony-Stimulating Factor-Inducing Activity)

First, an explanation will be provided regarding the method of obtaining the "antibodies or fragments which have granulocyte colony-stimulating factor-inducing activity" according to the invention. (Also referred to as "antibodies used for the invention" hereinafter throughout the present specification.)

The present inventors administered a mouse macrophage cell line as an immunogen to MRL/lpr mice (autoimmune mice), and isolated monoclonal antibodies. Then, the obtained monoclonal antibodies were applied to the mouse macrophage cell line and examined the effect of the antibodies to the macrophage cells. As a result, it was discovered that one of the obtained antibodies had the character of causing production of G-CSF by the mouse macrophage cell line in a concentration-dependent manner. (The hybridoma cell line that produces the antibody has been deposited as FERM BP-6103.)

Throughout the present specification, the term "monoclonal antibodies" will refer to monoclonal antibodies with reactivity to the macrophage cell line, and specifically refer to monoclonal antibodies with a function of causing production of G-CSF.

The antibodies used for the invention had the character to bind substantially to the macrophage cell line. The antibodies used for the invention include any polyclonal antibody or monoclonal antibody having this characters. The "monoclonal antibodies" include monoclonal antibodies belonging to all the immunoglobulin classes IgG, IgM, IgA, IgD and IgE, and are preferably monoclonal antibodies of the immunoglobulin classes IgG and IgM.

The macrophage cell line may be prepared from naturally occurring leukemia cells or it may be prepared by transformation with leukemia virus.

The antibodies used for the invention may be obtained according to a common procedure (for example, the method described in "Zoku Seikagaku Jikken Koza 5, Men'eki Seikagaku Kenkyuuhou" [Methods of Biochemical Experiments V-Immunobiochemistry Research Methods], ed. by The Japanese Biochemical Society: published by Tokyo Kagaku Dojin).

The monoclonal antibodies used for the invention can be produced from a hybridoma (fused cell line) created by cell fusion. The hybridoma that produces monoclonal antibodies is prepared by the following: the antibody-producing cells are fused with myeloma cells, and then the antibody-producing hybridoma is cloned by specific binding to the macrophage cell line. This procedure may be carried out according to conventionally known protocols except for the use of all or part of the macrophage cell line as the immunogen.

The immunogen used may be the macrophage cell line itself, or else there may be prepared a (poly)peptide solutions derived from all or a portion of the membrane fraction or soluble extract of the macrophage cell line, or a mixture thereof with Freund's complete adjuvant. The animals used as the object of immunization may be a mammal such as a mouse, rat, guinea pig, hamster or rabbit, and is preferably a mouse or rat, and more preferably a mouse. The immunization is carried out by one or several injections into the mammals through a subcutaneous, intramuscular, intravenous, foot pad or intraabdominal route.

Following initial immunization, 1-4 booster immunizations were carried out every 1-2 weeks interval, with a final immunization after another 1-4 weeks. The antibody-producing cells are collected from the immunosensitized animals after about 3-5 days from the final immunization.

The monoclonal antibodies used for the invention include the monoclonal antibodies produced by a hybridoma of "FERM BP-6103" (3-4H7 antibodies), their fragments and antibodies having essentially the same characters. "3-4H7 antibody" has the ability to induce G-CSF production by the cells.

The hybridoma that produces the monoclonal antibodies used for the invention may be prepared by a commonly known method. As an example of a commonly known method for preparation of a monoclonal antibody-secreting hybridoma, there may be mentioned in the methods of Koehler and Milstein (Nature, Vol. 256, pp. 495-497, 1975) or its modified methods. Here, the monoclonal antibodies are prepared by culturing fused cells (a hybridoma) that are obtained by fusing antibody-producing cells from a spleen, lymph node, bone marrow or tonsil, preferably a spleen, taken from an animal immunosensitized as described above, with myeloma cells from a mammalian animal such as a mouse, rat, guinea pig, hamster, rabbit or human, preferably of the same species, and more preferably from a mouse, rat, or human. The culturing may be carried out in vitro, or in vivo in the ascites fluid of a mammalian animal such as a mouse, rat, guinea pig, hamster or rabbit, preferably a mouse or rat, and more preferably a mouse, and the antibodies may be obtained from each culture supernatants or from the ascites fluid of the mammalian animal.

As examples of myeloma cell lines to be used for the cell fusion, there may be the mouse-derived myelomas "P3/X63-AG8", "P3/NSI/1-Ag4-1", "P3/X63-Ag8.U1", "SP2/0-Ag14", "PAI", "FO" or "BW5147", the rat-derived myeloma "210RCY3-Ag1.2.3" and the human-derived myelomas "U-266AR1", "GM1500-6TG-A1-2", "UC729-6", "CEM-AGR", "DlR11" and "CEM-T15".

The screening of fused cell clones that produce the monoclonal antibodies and used for the invention may be accomplished by measuring the antigen reactivity of the culture supernatants from the wells exhibiting cell growth in a microtiter plate using an enzyme-immunological method such as flow cytometry, RIA or ELISA.

As examples of basic media, there may be low calcium media such as Ham'F12 medium, MCDB153 medium or low calcium MEM medium, and high calcium media such as MCDB104 medium, MEM medium, D-MEM medium, RPMI1640 medium, ASF104 medium or RD medium. Serum, hormone cytokines and/or various organic or inorganic substances may be added to the basic medium depending on the purpose. Isolation and purification of the monoclonal antibodies from the culture supernatant or ascites fluid can be accomplished by various method such as saturated ammonium sulfate method, euglobulin precipitation, caproic acid method, caprylic acid method, ion-exchange chromatography (DEAE, DE52, etc.), affinity column chromatography with an anti-immunoglobulin column or Protein A or Protein G column, or hydrophobic chromatography.

The monoclonal antibodies used for the invention may also be obtained by any other method, without being restricted to the production method described above. Ordinary "monoclonal antibodies" have sugar chains with different structures depending on the types of a mammalian animal which has been immunosensitized, and the "monoclonal antibodies" used for the invention are not limited by structural differences in these sugar chains and include any monoclonal antibody derived from mammalian animals. The "monoclonal antibodies" used for the invention also include monoclonal antibodies produced by phage display, as well as human-type monoclonal antibodies obtained using transgenic mice created by genetic engineering that produce human-type antibodies by incorporation of human immunoglobulin genes, for example, chimeric monoclonal antibodies obtained by using gene recombination techniques to recombine the constant region (Fc region) of a mammalian animal-derived monoclonal antibody with the Fc region of a human monoclonal antibody, and humanized monoclonal antibodies obtained by recombining the complementarity-determining region (CDR) that can directly bind in a complementary manner with the antigen, with the corresponding region of a human monoclonal antibody.

According to the invention, an "antibody fragment" may also be used, where "antibody fragment" means an antibody fragment including at least one variable region, synonymous with the "antibody portion" mentioned in Japanese Patent Application HEI No. 9-266591. Specifically, it refers to the Fv, F(ab')2, Fab' or Fab fragments. Here, "F(ab')2" and "Fab'" refer to antibody fragments produced by treating an immunoglobulin (monoclonal antibody) with a protease such as pepsin or papain, and they are obtained by digestion before and after the sulfide bonds present between the two H chains at the hinge region. For example, treatment of IgG with papain cleaves it upstream from the disulfide bonds present between the two H chains at the hinge region, producing two homologous antibody fragments each comprising an L chain composed of a VL (L chain variable region) and CL (L chain constant region) and an H chain fragment composed of a VH (H chain variable region) and CHγ1 (γ1 region of the H chain constant region) which are bonded by sulfide bonds at the C-terminal region. These two homologous antibody fragments are each designated as Fab'. Treatment of IgG with pepsin cleaves it down-stream from the disulfide bonds present between the two H chains at the hinge region, producing an antibody fragment which is slightly larger than just the aforementioned two Fab' fragments connected at the hinge region. This antibody fragment is designated as F(ab')2.

The protein encoded by the gene of the invention is characterized by binding to an antibody or its fragment that is active to induce granulocyte colony-stimulating factor, as explained in detail above. The term "binding" as used throughout the present specification means ordinary binding between a protein and antibody, and it may be measured using common immunological analysis techniques (for example, immunoprecipitation, ELISA, immunoblotting, etc.)

(Gene of the Invention)

The present invention provides a gene which encodes the protein having the amino acid sequence listed as SEQ ID NO:1 of the Sequence Listing or a protein which is homologous thereto. The invention also provides a gene having the nucleotide sequence listed as SEQ ID NO:1 of the Sequence Listing or a nucleotide sequence which is homologous thereto.

There are no particular restrictions on the type of the gene of the invention, and it may be naturally occurring DNA, recombinant DNA or chemically synthesized DNA, or even a genomic DNA clone or a cDNA clone.

The gene of the invention will typically have the nucleotide sequence listed as SEQ ID NO:1 of the Sequence Listing, but this is only the sequence of a clone (MMR19) obtained in the following examples to represent an embodiment of the invention. Those skilled in the art are well aware that natural genes have a small number of variations depending on the breeding conditions of the biological species that produce it, and on the ecosystem, or on the presence of highly similar isozymes. Consequently, the "gene" of the invention is not limited to the gene having the nucleotide sequence listed as SEQ ID NO:1 of the Sequence Listing but also includes all genes encoding proteins having the characters described in the present specification.

In particular, disclosure by the present specification of the amino acid sequence for the protein of the invention and the DNA sequence encoding the protein easily allows to isolate a gene encoding a protein with similar physiological activity from another biological species by utilizing basic genetic engineering techniques such as hybridization or PCR. Genes obtained in this manner are also within the scope of the present invention.

There are no particular restrictions for the hybridization conditions used for screening of a homologous gene, and they may be appropriately selected by a person skilled in the art depending on the degree of homology between the target homologous gene and probe, although stringent conditions are generally preferred, and for example, the hybridization conditions may be 6×SSC [0.9 M NaCl, 0.09 M sodium citrate (pH 7.0)], 5× Denhardt's solution [1 g ficoll, 1 g polyvinyl pyrrolidone, 1 g BSA in 1000 mL], 0.5-% SDS, 25° C.-68° C. (for example, 37° C., 42° C. or 68° C.), or 0-50% formamide, 6×SSC, 0.5% SDS, 25-68° C. (for example, 37° C., 42° C. or 68° C.). It is well known to those skilled in the art that appropriate setting of the hybridization conditions including the formamide concentration, Denhardt's solution concentration, salt concentration, temperature, etc. will allow to clone DNA containing a nucleotide sequence with a given degree of homology or greater, and all homologous genes cloned in this manner are within the scope of the present invention.

A homologous gene cloned by hybridization in this manner has at least 70%, preferably at least 80%, more preferably at least 90%, even more preferably at least 95% and most preferably at least 98% homology with respect to the nucleotide sequence listed as SEQ ID NO:1 of the Sequence Listing.

(Protein of the Invention)

The present invention provides the protein having the amino acid sequence listed as SEQ ID NO:1 of the Sequence Listing or a protein homologous thereto.

The protein having the amino acid sequence listed as SEQ ID NO:1 of the Sequence Listing according to the invention may be obtained by incorporating the gene encoding therefor into an appropriate expression vector, transforming this vectors to an appropriate host and expressing the recombinant protein. However, the source and preparation method are not restricted so long as the protein of the invention has the characters described in the present specification, and it may be a naturally produced protein, a protein expressed from recombinant DNA by a genetic engineering method or a protein chemically synthesized.

The protein of the invention will typically have the sequence of 241 amino acids listed as SEQ ID NO:1 of the Sequence Listing. However, those skilled in the art are well aware that natural proteins include variations of one or more amino acids due to gene variation depending on the breeding conditions of biological species that produce it, on the ecosystem, the presence of highly similar isozymes. The term "amino acid variation" as used here means one or more amino acid substitutions, deletions, insertions and/or additions. The "protein" of the invention has the amino acid sequence listed as SEQ ID NO:1 based on deduction from the nucleotide sequence of the cloned gene, but it is not limited only to proteins with that sequence and is intended to include all homologous proteins that have the characteristics described in the present specification. The homology is at least 50%, preferably at least 60%, more preferably at least 70%, more preferably at least 80%, even more preferably at least 90%, yet more preferably at least 95% and most preferably at least 98%.

Generally speaking, introduction of a substitution between amino acids with the same nature (for example, a substitution between two hydrophobic amino acids, a substitution between two hydrophilic amino acids, a substitution between two acidic amino acids or a substitution between two basic amino acids) will usually tend to give a varied protein with the same characters as the original protein. Those skilled in the art are familiar with methods of preparing recombinant proteins with desired characters using gene recombinant techniques, and such varied proteins are also within the scope of the invention.

The following examples in the present specification describe cloning of mouse macrophage-derived cDNA as an embodiment of the invention. The use of the amino acid sequence of the protein disclosed in the present specification or the sequence of the (mouse-derived) gene coding therefor, or a portion thereof, for isolation of a gene encoding a protein from another source but having similar physiological activity using gene engineering techniques such as hybridization or PCR, is within the scope of commonly accepted knowledge to a person skilled in the art, and proteins encoded by such isolated genes are also within the scope of the present invention.

(Human-Type Gene and Protein)

For example, the following method may be mentioned as an example of obtaining a human-derived homologue of the gene and protein of the invention.

The total RNA is extracted from a human macrophage cell line (THP-1, U937, HL-60) by guanidium thiocyanate-phenol-chloroform single-step extraction (Laboratory Manuals of Genetic Engineering, 3rd Edition, pp. 83-84, 1996), and purified using an oligo(dT) cellulose column, to obtain poly(A)$^+$ RNA. Reverse transcriptase (MMLV-RTase) and DNA polymerase are used to synthesize double-stranded cDNA. The double-stranded cDNA is used to construct a cDNA library using a λZAPII phage vector by the method of Gubler-Hoffmann (Gubler, U. and Hoffmann, B. J.: Gene, 25:263-269, 1983). A probe is then prepared by amplifying a DNA sequence using a primer DNA that can amplify a sequence in the region of the nucleotide sequence SEQ ID NO:1) of the mouse cDNA (MMR19 clone) disclosed in the present specification, having high homology with the human sequence (for example, the region from position 172 to position 241 of SEQ ID NO:1 which has been found to have 91% homology with the human sequence) and the template DNA from the human macrophage cell cDNA library. Or region (for example, the region from position 172 to position 241 of SEQ ID NO:1) is used directly as the probe for screening the cDNA encoding the entire length of the target protein from the human macrophage cell cDNA library. The cDNA nucleotide sequence is analyzed by the Primer Walking method. The cDNA confirmed to encode the entire length of the target protein is introduced into a baculovirus to express a protein, which can be purified with an affinity column to obtain the human-type homologous protein.

As explained above, the present invention relates to the gene or protein having the nucleotide sequence listed as SEQ ID NO:1 or the amino acid sequence listed as SEQ ID NO:2, and to genes and proteins which are homologous thereto. As a result of a search to determine whether or not sequences homologous to the nucleotide sequence listed as SEQ ID NO:1 and the amino acid sequence listed as SEQ ID NO:2 provided by the invention are present in other organisms, it was confirmed that human ESTs (expressed sequence tags) include sequences having high homology with the gene of the invention (see Example 3 below). It will therefore be readily appreciated that the human-derived homologous gene can also be isolated by screening of a human-derived gene library (cDNA library, etc.) using the human-derived ESTs having high homology with the nucleotide sequence of the invention as the probe.

As described above, a database search revealed that portions (i.e. DNA fragments) of the nucleotide sequence listed as SEQ ID NO:1 according to the invention are conserved, having high homology with the human sequence. Such DNA fragments are useful as probes for screening of the human-derived homologous gene, and therefore constitute one aspect of the present invention. The DNA fragments include DNA fragments containing the nucleotide sequence from position 519 to position 736, the nucleotide sequence from position 666 to position 689, the nucleotide sequence from position 381 to position 403 or the nucleotide sequence from position 709 to position 727 of the nucleotide sequence listed as SEQ ID NO:1 of the Sequence Listing, while DNA fragments containing a nucleotide sequence which is any of these nucleotide sequences with one or more nucleotide deletions, substitutions, additions or insertions or a nucleotide sequence which has at least 80%, preferably at least 85%, more preferably at least 90%, even more preferably at least 95% and most preferably at least 98% homology with any of these nucleotide sequences, are also within the scope of the invention.

A database search also revealed that a portion of the amino acid sequence listed as SEQ ID NO:2 according to the invention is conserved with high homology in the human sequence. Protein fragments comprising portions of the protein of the invention are also useful as reagents for analysis and isolation of antibodies with G-CSF inducing activity, as is the protein of the invention, and also have potential utility as a drug like the protein of the invention, and thus constitute an aspect of the invention.

The mentioned proteins include the amino acid sequences from residues 1 to 91, 50 to 146, 1 to 78, 200 to 241, 172 to 241, 103 to 150, and 169 to 241 of the amino acid sequence listed as SEQ ID NO:2 of the Sequence Listing, while proteins containing an amino acid sequence which is any of these amino acid sequences with one or more amino acid deletions, substitutions, additions or insertions or an amino acid sequence having at least 70%, preferably at least 80%, more preferably at least 85%, even more preferably at least 90%, even more preferably at least 95% and most preferably at least 98% homology with any of these amino acid sequences, are also within the scope of the invention.

The present inventors have determined the nucleotide sequence of the human-type antigen gene by a method similar to the one described above (see Example 4 below). Consequently, the present invention provides a gene having the nucleotide sequence listed as SEQ ID NO:3 of the Sequence Listing or having a nucleotide sequence which is homologous thereto. The invention also provides a protein having the amino acid sequence listed as SEQ ID NO:4 of the Sequence Listing or a protein which is homologous thereto. Here, "homologous" means that the scope of the invention is not limited to the gene having the nucleotide sequence listed as SEQ ID NO:3 or the protein having the amino acid sequence listed as SEQ ID NO:4, as was explained in the part of "Gene of the invention" and "Protein of the invention" described above.

(Antibodies of the Invention)

The invention also provides antibodies against the above-mentioned protein of the invention (also referred to hereinafter in the present specification as "monoclonal antibodies of the invention"). An example of the antibodies of the invention and a method for obtaining them is explained in detail.

The antibodies of the invention may be either poly-clonal antibodies or monoclonal antibodies, and in the case of monoclonal antibodies they may be chimeric antibodies. Mouse/human chimeric antibodies are particularly preferred. The "monoclonal antibodies" include monoclonal antibodies belonging to all the immunoglobulin classes such as IgG, IgM, IgA, IgD and IgE, and are preferably monoclonal antibodies of the immunoglobulin classes IgG and IgM.

The protein of the invention used as the antigen may be obtained by incorporating a gene encoding it into an appropriate expression vector, transforming the incorporated vector to an appropriate host and expressing the recombinant protein. The immunogen used may be, for example, an actual macrophage cell line or the membrane fraction of a macrophage cell line.

The antibodies of the invention, such as polyclonal antibodies (antiserum) or monoclonal antibodies may be obtained according to a common procedure (for example, the method described in "Zoku Seikagaku Jikken Koza 5, Men'eki Seikagaku Kenkyuuhou" [Method of Biochemical Experiments V-Immunobiochemistry Research Methods], ed. by The Japanese Biochemical Society: published by Tokyo Kagaku Dojin).

Specifically, a mammalian animal, preferably a mouse, rat, hamster, guinea pig, rabbit, dog, cat, pig, goat, horse or cow, and more preferably a mouse, rat, hamster, guinea pig or rabbit, is immunized with the antigen in combination with Freund's adjuvant if necessary. Polyclonal antibodies may be collected from serum obtained from the immunosensitized animal. Monoclonal antibodies may be produced from a hybridoma made of fusions between antibody-producing cells obtained from the immunosensitized animal and a myeloma cell line (myeloma cells) which has no ability to produce antibodies. The hybridoma was cloned the hybridoma and selected clones that produce monoclonal antibodies exhibiting specific affinity toward the antigen used to immunize the mammalian animal.

Specifically, the monoclonal antibodies may be produced in the following manner. The protein of the invention or cells expressing the protein of the invention are used as the immunogen together with Freund's adjuvant if necessary. For immunosensitization, a mouse, rat, hamster, guinea pig or rabbit, and preferably a mouse, rat or hamster (such animals include transgenic animals created to produce antibodies of other animals, such as human antibody-producing transgenic mice) is used by one or several injections through a subcutaneous, intramuscular, intravenous, foot pad or intraabdominal route, or by transplantation. Usually 1 to 4 booster immunizations are given every 1 to 14 days from the initial immunization, and 1 to 5 days after the final immunization, and the antibody-producing cells are taken from the immunosensitized mammalian animal.

The monoclonal antibodies of the invention may be produced from a hybridoma (fused cells) produced by cell fusion.

The hybridoma producing the monoclonal antibodies can be prepared by a commonly known method. As a commonly known method, it may be mentioned in the method of Koehler and Milstein (Nature, Vol. 256, pp. 495-497, 1975) or methods with modifications of that method. Specifically, the monoclonal antibodies are prepared by culturing fused cells (a hybridoma), which are obtained by fusing antibody-producing cells from a spleen, lymph nodes, bone marrow or tonsils, preferably a spleen, taken from an animal immunosensitized in the manner described above, with myeloma cells from a mammalian animal such as a mouse, rat, guinea pig, hamster, rabbit or human, and preferably from a mouse, rat, or human.

As examples of myeloma cell lines used for the cell fusion, there may be the mouse-derived myelomas as mentioned above, such as "P3/X63-AG8", "P3/NSI/1-Ag4-1", "P3/X63-Ag8.U1", "SP2/0-Ag14", "X63,653", "PAI", "FO" or "BW5147", the rat-derived myeloma "210RCY3-Ag1.2.3" and the human-derived myelomas "U-266AR1", "GM1500-6TG-A1-2", "UC729-6", "CEM-AGR", "DlR11" and "CEM-T15".

Screening of fused cell clones that produce the monoclonal antibodies used for the invention may be accomplished by culturing the fused cells in a microtiter plate, for example, and by using flow cytometry, RIA, ELISA alternative the like to measure the antigen reactivity of the culture supernatants from the wells exhibiting growth.

Production of monoclonal antibodies from the hybridoma may be carried out by culturing the hybridoma in vitro, or in vivo in the ascites fluid of a mouse, rat, guinea pig, hamster or rabbit, preferably a mouse or rat, and more preferably a mouse, and isolating the antibodies from the resulting culture supernatant or from the ascites fluid of the mammalian animal. In the case of in vitro culture, the hybridoma may be grown, maintained and stored following a condition varied depending on the properties of the cell line being cultured, the purpose of research and the culturing method. And the culturing used for production of monoclonal antibodies in culture supernatants may be carried out using a known nutrient medium or any nutrient medium derived and prepared from a known basic medium.

As examples of basic media, there may be the low calcium media such as Ham'F12 medium, MCDB153 medium or low calcium MEM medium, and high calcium media such as MCDB104 medium, MEM medium, D-MEM medium, RPMI1640 medium, ASF104 medium or RD medium. Serum, hormone cytokines and/or various organic or inorganic substances may also be added to the basic medium, depending on the purpose. Isolation and purification of the monoclonal antibodies can be accomplished by apply a saturated ammonium sulfate method, euglobulin precipitation, caproic acid method, caprylic acid method, ion-exchange chromatography (DEAE, DE52, etc.), affinity column chromatography with an anti-immunoglobulin column or Protein A or Protein G column, or else subjecting them to hydrophobic chromatography to subjecting the culture supernatant or ascites fluid.

A "chimeric antibody" according to the invention is a monoclonal antibody created by genetic engineering, and specifically, it refers to a chimeric monoclonal antibody such as a mouse/human chimeric monoclonal antibody, which is characterized as the monogbulin gene whose variable region is a mouse immunoglobulin variable region and the constant region is a human immunoglobulin constant region. The human immunoglobulin constant region is characterized to have an amino acid sequence depending on the isotype IgG, IgM, IgA, IgD or IgE, and the constant region of the recombinant chimeric monoclonal antibody of the invention may be the constant region of a human immunoglobulin belonging to any of the isotypes. It is preferably the constant region of human IgG. The chimeric monoclonal antibody of the invention may be produced, for example, in the following manner. It will be appreciated without mention, however, that the production method is not limited to the one described below.

For example, a mouse/human chimeric monoclonal antibody may be prepared with reference to Jikken Igaku (Experimental Medicine) (special issue) I, Vol. 6, N.10, 1988 and Japanese Examined Patent Publication HEI No. 3-73280. That is, it may be prepared by inserting into one or separate expression vectors the CH gene (C gene encoding the H chain constant region), taken from DNA encoding human immunoglobulin, downstream from the active $V_H$ gene (rearranged VDJ gene encoding the H chain variable region) taken from DNA encoding the monoclonal antibody isolated from the mouse monoclonal antibody-producing hybridoma, and the $C_L$ gene (C gene encoding the L chain constant region) taken from DNA encoding human immunoglobulin, downstream from the active $V_L$ gene (rearranged $V_J$ gene encoding L chain variable region) taken from DNA encoding the monoclonal antibody isolated from the same hybridoma, with each arranged in an expressible manner, transforming host cells with the expression vector and culturing the transformed cells.

Specifically, first a DNA is extracted from the mouse monoclonal antibody-producing hybridoma by a common procedure, and then the DNA is digested with appropriate restriction endonucleases (for example, EcoRI, HindIII, etc.) and the digested fragments are subjected to electrophoresis (for example, using a 0.7% agarose gel) for Southern blotting. The electrophoresed gel is stained with ethidium bromide, for example, and photographed, after the marker positions are attached, and the gel is washed twice and then immersed for 15 minutes in a 0.15 M HCl solution. It is then immersed for 10 minutes in a 0.4 N NaOH solution with gentle shaking. A common method is used for transfer the DNA to a filter, recovery of the filter. After 4 hours, the filter is washed twice with 2×SSC. After thoroughly drying the filter, it is baked (75° C., 3 hours). Upon completion of baking, the filter is placed in a 0.1×SSC/0.1% SDS solution and incubated at 65° C. for 30 minutes. It is then immersed in a 3×SSC/0.1% SDS solution. The obtained filter is placed in a plastic bag together with the prehybridization solution, and incubated at 65° C. for 3-4 hours.

Next, $^{32}$P-labelled probe DNA and hybridization solution are added for reaction at 65° C. for about 12 hours. After completion of hybridization, the filter is washed with an appropriate salt concentration, reaction temperature and time (for example, 2×SSC, 0.1% SDS solution, room temperature, 10 minutes). The filter is placed in a plastic bag, a small amount of 2×SSC is added, the bag is sealed, and autoradiography is performed. This Southern blot method allows identification of the rearranged VDJ gene and VJ gene encoding the H chain and L chain of the mouse monoclonal antibody, respectively. The zones containing the DNA fragments identified by the method described above are fractionated by sucrose density gradient centrifugation and the isolated DNA is incorporated into a phage vector (for example, charon4A, charon28, λEMBL3, λEMBL4, etc.), and then E. coli (for example, LE392, NM539, etc.) is transformed with the phage vector, and a genomic library is created. The genomic library is used for plaque hybridization according to the method of Benton and Davis (Science, Vol. 196, pp. 180-182(1977)) using the appropriate probe (H chain J gene, L chain (κ) J gene, etc.), and the positive clones containing either the rearranged VDJ gene or VJ gene are obtained. Restriction enzyme maps of the obtained clones are prepared and the nucleotide sequences are determined to confirm that the obtained genes contain the target rearranged $V_H$ (VDJ) gene or $V_L$ (VJ) gene.

Separately, the human $C_H$ gene and human $C_L$ gene used for chimerization are isolated. For example, when creating a chimera with human IgG1, the Cγ1 gene as the $C_H$ gene and the Cη gene as the $C_L$ gene are isolated. By taking advantage of the high homology between the nucleotide sequences of the mouse immunoglobulin genes and human immunoglobulin genes, these genes can be obtained using as probes the mouse Cγ1 gene and mouse Cκ gene, which correspond to the human Cγ1 gene and human Cκ gene for their isolation from a human genomic library.

Specifically, the 3 kb HindIII-BamHI fragment from clone Ig146 (Proc. Natl. Acad. Sci. USA, Vol. 75, pp. 4709-4713(1978)) and the 6.8 kb EcoRI fragment from clone MEP10 (Proc. Natl. Acad. Sci. USA, Vol. 78, pp. 474-478(1981)) are used as probes to isolate a DNA fragment containing the human κ gene containing the enhancer region, which is derived from a human λCharon4A HaeIII-AluI genomic library (Cell, Vol. 15, pp. 1157-1174(1978)). The human Cγ1 gene is isolated, for example, by digesting human embryonic liver cell DNA with HindIII, fractionating by agarose gel electrophoresis, and inserting the 5.9 kb band in λ788 and using the aforementioned probes.

The mouse $V_H$ gene and mouse $V_L$ gene and the human $C_H$ gene and human $C_L$ gene obtained in this manner are incorporated into an expression vector, such as pSV2gpt or pSV2neo by a common procedure, using an appropriate restriction endonuclease and DNA ligase, taking into account the promoter region and enhancer region, so that the human $C_H$ gene is placed downstream from the mouse $V_H$ gene and the human $C_L$ gene is placed downstream from the mouse $V_L$ gene. Here, the chimeric genes of the mouse $V_H$ gene/human $C_H$ gene and mouse $V_L$ gene/human $C_L$ gene may be arranged simultaneously in the same expression vector, or they may be arranged in separate expression vectors.

The expression vector inserting the chimeric gene constructed in this manner is then introduced into myeloma cells such as P3X63-Ag8-653 cells or SP210 cells, which do not of themselves produce antibodies, by the protoplast fusion method, DEAE-dextrin method, calcium sulfate method, electroporation or the like. The transformed cells are selected out by culturing in medium containing a drug corresponding to the drug resistance gene, which is introduced into the expression vector, and the target chimeric monoclonal antibody-producing cells are isolated. The target chimeric monoclonal antibodies are taken from the culture supernatant of the selected antibody-producing cells.

The "human-type antibodies (CDR-grafted antibodies)" according to the invention are monoclonal antibodies prepared by genetic engineering, and specifically, they are human-type monoclonal antibodies characterized in that all or a portion of the complementarity-determining region of the hypervariable region is the complementarity-determining region of the hypervariable region derived from the mouse monoclonal antibody, the framework region of the variable region is the framework region of the variable region derived from the human immunoglobulin, and the constant region is the human immunoglobulin region.

The complementarity-determining regions are the three regions found in the hypervariable region of the variable region of the antibody, which are the sites of direct complementary binding to the antigen (CDRs: complementarity-determining regions; CDR1, CDR2, CDR3), and the variable framework regions are the four regions lying before and after the three complementarity-determining regions, which are relatively conserved (Framework regions: FR1, FR2, FR3, FR4). Stated differently, this means a monoclonal antibody wherein all of the regions except for all or a portion of the complementarity-determining region of the hypervariable region of the mouse monoclonal antibody are repieced by the corresponding regions of the human immunoglobulin. The constant region derived from the corresponding region of the human immunoglobulin has the amino acid sequence characteristic of each isotype IgG, IgM, IgA, IgD or IgE, and the constant region of the human-type monoclonal antibodies of the invention may be the constant region of human immunoglobulin belonging to any isotype, preferably the constant region of human IgG. There are also no restrictions on the framework regions in the variable region derived from the human immunoglobulin.

The human-type monoclonal antibodies of the invention may be produced, for example, in the following manner, with understanding that there is no limitation to this production method. For example, the recombinant human-type monoclonal antibodies derived from mouse monoclonal antibodies may be prepared by genetic engineering with reference to Japanese Patent Public Inspection HEI No. 4-506458 and Japanese Unexamined Patent Publication SHO No. 62-296890. That is, at least one mouse H chain CDR gene and at least one mouse L chain CDR gene paring to the mouse H chain CDR gene are isolated from the mouse monoclonal antibody-producing hybridoma, and a human H chain gene encoding the entire region other than the human H chain CDR corresponding to the mouse H chain CDR and the human L chain encoding the entire region other than the human L chain CDR corresponding to the mouse L chain CDR are isolated from the human immunoglobulin gene.

The isolated mouse H chain CDR gene and human H chain gene are introduced in an expressible manner into an appropriate expression vector, and likewise the mouse L chain CDR gene and the human L chain gene are introduced in an expressible manner into another appropriate expression vector. Alternatively, the mouse H chain CDR gene/human H chain gene and the mouse L chain CDR gene/human L chain gene may be introduced in an expressible manner into the same expression vector. By transforming host cells with the expression vector prepared in this manner, it is possible to obtain human-type monoclonal antibody-producing transformants, and by culturing these transformants, it is possible to obtain the target human-type monoclonal antibodies from the culture supernatant.

A "human antibody" according to the invention is an immunoglobulin wherein all of the regions of the immunoglobulin including the H chain variable region and H chain constant region and the L chain variable region and L chain constant region are derived from a gene encoding a human immunoglobulin. Human antibodies may be produced by the same method used to prepare polyclonal antibodies or monoclonal antibodies described above. For example, human antibodies are made by immunosensitization of a transgenic animal, which was created by incorporating at least a human immunoglobulin gene into the gene locus of a non-human mammalian animal, such as a mouse, according to a common procedure. For example, a human antibody-producing transgenic mouse can be created according to the procedure described in Nature Genetics, Vol. 7, pp. 13-21, 1994; Japanese Patent Public Inspection HEI No. 4-504365; International Patent Disclosure WO94/25585; Nikkei Science, No.6, pp. 40-50, 1995; Nature, Vol. 368, pp. 856-859, 1994; or Japanese Patent Public Inspection HEI No. 6-500233.

"Antibody portion" according to the invention means an antibody fragment containing at least one variable region, and refers to a partial region of an antibody, preferably a monoclonal antibody, according to the invention mentioned above; specifically, it refers to the Fv, F(ab')$_2$, Fab' or Fab fragments. Here, "F(ab')$_2$" and "Fab'" refer to antibody fragments produced by treating an immunoglobulin (monoclonal antibody) with a protease such as pepsin or papain, and they are obtained by digestion before and after the sulfide bonds present between the two H chains at the hinge region. For example, treatment of IgG with papain cleaves it upstream from the disulfide bonds present between the two H chains at the hinge region, resulted in producing two homologous antibody fragments, each consisting of an L chain composed of a $V_L$ (L chain variable region) and $C_L$ (L chain constant region) and an H chain fragment composed of a $V_H$ (H chain variable region) and $C_H\gamma1$ (γ1 region of the H chain constant region), which are bonded by sulfide bonds at the C-terminal region. These two homologous antibody fragments are both designated as Fab'. Treatment of IgG with pepsin cleaves it downstream from the disulfide bonds present between the two H chains at the hinge region, resulted in producing an antibody fragment which is slightly larger than the aforementioned two Fab' fragments connected at the hinge region. This antibody fragment is designated as F(ab')$_2$.

(Recombinant Vector and Transformant)

The present invention further provides a recombinant vector containing the gene or DNA fragment of the invention.

The recombinant vector may be prepared by linking the gene of interest to a recombination vector which is readily available to those skilled in the art (for example, plasmid DNA or the like) by a common procedure. Examples of vectors to be used include, but are not limited to, pBluescript, pUC18, pUC19 and pBR322, as plasmids derived from E. coli.

An expression vector is particularly useful for the purpose of producing a protein of interest. The type of expression vector is not particularly restricted so long as it has the function of expressing the gene of interest in host cells, either or both prokaryotic cells and eukaryotic cells, to produce the protein of interest. For example, pQE-30, pQE-60, pMAL-C2, pMAL-p2 and pSE420 are preferred as expression vectors for E. coli, pYES2 (Saccharomyces) and pPIC3.5K, pPIC9K, pAO815 (all of genus Pichia) as expression vectors for yeast, and pBacPAK8/9, pBK283, pVL1392 and pBlueBac4.5 as expression vectors for insects.

As an example of a method for incorporating a gene fragment of the invention into a vector such as a plasmid, there may be the procedure described in "Sambrook, J. et al., Molecular Cloning, A Laboratory Manual, (Second edition), Cold Spring Harbor Laboratory, 1. 53(1989)". A commercially available ligation kit (for example, by Takara Shuzo) can be conveniently used. The recombinant vector (recombinant plasmid, for example) obtained in this manner may be introduced into host cells by the method described below.

Introduction of a recombinant vector of the invention into host cells (transformation or transfection) can be accomplished by a conventionally known protocol, and as examples, there may be the calcium chloride method or calcium chloride/rubidium chloride method, electroporation, electroinjection, chemical treatment with PEG or the like, a method using a gene gun, etc., as described in "Sambrook, J. et al., Molecular Cloning, A Laboratory Manual, (Second edition), Cold Spring Harbor Laboratory, 1. 74(1989)". Alternatively, the transformation may be accomplished by the method of Cohen et al. [Proc. Natl. Acad. Sci. USA, 69, 2110(1972)], the protoplast method [Mol. Gen. Genet., 168, 111(1979)] or the competent method [J. Mol. Biol., 56, 209(1971)], for example, when the host cells are bacteria (*E. coli, Bacillus subtilis*, etc.); by the method of Hinnen et al. [Proc. Natl. Acad. Sci. USA, 75, 1927(1978)] or the lithium method [J. Bacteriol., 153, 163(1983)], for example, when the host cells are *Saccharomyces cerevisiae*; by the leaf disk method [Science, 227, 129(1985)] or the electroporation method [Nature, 319, 791(1986)], for example, when the host cells are plant cells; by the method of Graham [Virology, 52, 456(1973)], for example, when the host cells are animal cells; or by the method of Summers et al. [Mol. Cell. Biol., 3, 2156-2165 (1983)], for example, when the host cells are insect cells.

There are no particular restrictions on the host cells to be used to create the transformants so long as they can accommodate and be transformed by the recombinant vector of the invention. Various types of cells may be used, such as naturally existing cells or artificially established recombinant cells, as are commonly used in the technical field of the invention. For example, there may be mentioned prokaryotic cells such as bacteria (*Escherichia, Bacillus*) and the like, lower eukaryotic cells including monocellular hosts such as yeast (*Saccharomyces, Pichia*) and the like, and higher eukaryotic cells such as silkworm cells and the like. The host cells are preferably *E. coli*, yeast or insect cells, with specific examples including *E. coli* (M15, JM109, BL21, etc.), yeast (INVSc1 (Saccharomyces), GS115, KM71 (both of *Pichia*), etc.), and insect cells (BmN4, silkworm larva, etc.). Examples of animal cells include mouse-derived, *Xenopus laevis*-derived, rat-derived, hamster-derived, monkey-derived and human-derived cells, or cultured cell lines established from these cells.

When the host cells are bacteria, particularly *E. coli*, they will usually include at least the expression vector, which has the promoter/operator region, an initiation codon, the gene encoding the protein of interest, a termination codon, a terminator and a replicable unit. When the host cells are yeast, plant cells, animal cells or insect cells, they will usually include at least the expression vector and preferably a promoter, initiation codon, the gene encoding the protein of interest, a termination codon and a terminator. As appropriate, they may also contain, DNA encoding the signal peptide, an enhancer sequence, the non-translated regions at the 5' and 3' ends of the gene of interest, a selection marker region or a replicable unit.

The preferred initiation codon for the vector of the invention is the methionine codon (ATG). Examples of termination codons are the ordinary termination codons (for example, TAG, TGA and TAA).

A replicable unit means DNA with the ability to replicate its entire DNA sequence in the host cells, and this includes natural plasmids, artificially modified plasmids (plasmids prepared from natural plasmids) and synthetic plasmids. As preferred plasmids, there may be plasmids pQE30, pET and PCAL or their artificially modified forms (DNA fragments obtained by treating pQE30, pET or pCAL with an appropriate restriction endonuclease), for *E. coli*, plasmids pYES2 and pPIC9K for yeast or plasmid pBacPAK8/9 for insect cells.

The enhancer sequence and terminator sequence used may be ones commonly used by those skilled in the art, such as the ones derived from SV40. The selection marker may be a common one used following an ordinary method. Examples thereof include resistance genes against antibiotics, such as tetracycline, ampicillin, kanamycin, neomycin, hygromycin, spectinomycin or chloramphenicol.

The expression vector may be prepared by linking the aforementioned promoter, initiation codon, gene encoding the protein of interest, termination codon and terminator region in a continuous and cyclic manner in the appropriate replicable unit. Here the appropriate DNA fragments (for example, linkers, other restriction enzyme sites, etc.) may be used following a common procedure, such as digestion with a restriction enzyme and ligation using T4DNA ligase, as desired.

(Receptor, Screening Method, Novel Substance)

The protein encoded by the gene of the invention may possibly act at the entry point of induction and stimulation of G-CSF. (That is, while the present invention is not restricted in any way by the following theory, one possible explanatory model is that binding of an external ligand to the protein of the invention residing on the surface layer of macrophage cells, transmitting of the resulting signal into the cell, and leading to release of G-CSF by the macrophage.) Consequently, the protein of the invention could be the receptor working as a granulocyte colony-stimulating factor-inducer or a portion thereof. A "portion of a receptor" would include a subunit of the receptor, possibly modified with a sugar chain or the like. The receptor has the ability to bind (also known as "affinity") to substances that can allow to induce production of granulocyte colony-stimulating factor, such as monoclonal antibodies produced by the hybridoma deposited as FERM BP-6103 or their fragments, and it may possibly reside in the cell membrane of cells capable of producing granulocyte colony-stimulating factor, including macrophages. The present invention provides such a receptor.

The invention further provides a useful substance screening method by using the protein of the invention. Such a screening method includes measurement of binding between the substance of interest and the protein of the invention, or the receptor, measurement of the effect of the substance of interest via the receptor (for example, production of G-CSF by the macrophages or production of a marker substance from appropriately transformed cells), or comparison between the structure of the substance of interest (for example, its amino acid sequence when the substance of interest is a protein) and the structure of the protein of the invention (for example, its amino acid sequence).

The protein of the invention used for screening is preferably (a) a protein having the amino acid sequence listed as SEQ ID NO:4 of the Sequence Listing; (b) a protein having the amino acid sequence listed as SEQ ID NO:4 of the Sequence Listing with one or more amino acid deletions, substitutions, additions or insertions and also binding to an antibody or its fragment that is active to induce granulocyte colony-stimulating factor; (c) a protein having at least 50% (preferably at least 60%, more preferably at least 70%, even more preferably at least 80%, even more preferably at least 90%, especially preferably at least 94% and most preferably at least 98%) homology with the amino acid sequence listed as SEQ ID NO:4 and also binding to an antibody or its fragment that is active to induce granulocyte colony-stimulating factor; or (d) a protein that is encoded by DNA which hybridizes with DNA having the nucleotide sequence listed as SEQ ID NO:3 of the Sequence Listing under stringent conditions and that binds to an antibody or its fragment that is active to induce granulocyte colony-stimulating factor.

The following is a more specific example of the screening method: A vector is constructed by inserting the G-CSF promoter gene and a gene encoding a marker protein, such as luciferase, β-galactosidase, Green Fluorescent Protein (GFP), β-lactamase or chloramphenicol acetyltransferase (CAT), at downstream thereof, and a drug resistance gene against a drug, such as tetracycline, ampicillin, kanamycin, neomycin, hygromycin or spectinomycin, at further downstream thereof. The vector is introduced into cells (for example, a macrophage cell line, and preferably a human-derived macrophage cell line) bearing receptors, which contains the protein of the invention. The obtained cells are treated with a drug-containing medium, and colony-forming cells are selected. Clones expressing the marker protein upon induction are then selected. It is then confirmed that expression of the marker protein reflects actual expression of G-CSF mRNA. The transformed cell line obtained in this manner is treated with various substances, followed by screening for substances that have induced expression of the marker protein.

A useful substance obtained by screening is (a) a substance which can bind to the receptor, and as a result of its binding to the receptor, it can elicit a structural change in the receptor, transmit signals into the cell via the receptor, and induce production of granulocyte colony-stimulating factor (also known as an "agonist" or "agent"); (b) a substance which can bind to the receptor, and as a result of its binding to the receptor, it can inhibit the binding of the receptor to the substances that can induce production of granulocyte colony-stimulating factor, but it in itself does not induce production of granulocyte colony-stimulating factor (also known as an "antagonist" or "blocker"); or (c) a substance which can bind to the receptor, and as a result of its binding to the receptor, it can inhibit the binding of the receptor to the substances that can induce production of granulocyte colony-stimulating factor, but it in itself blocks production of granulocyte colony-stimulating factor (also known as an "inverse agonist" or "reagent").

Such substances are novel. Thus, the present invention also provides (a) a substance which can bind to the receptor, and as a result of its binding to the receptor, it can induce a change in the receptor, transmit signals into the cell via the receptor, and induce production of granulocyte colony-stimulating factor; (b) a substance which can bind to the receptor, and as a result of its binding to the receptor, it can inhibit the binding of the receptor to the substances that can induce production of granulocyte colony-stimulating factor, but it in itself does not induce production of granulocyte colony-stimulating factor; and (c) a substance which can bind to the receptor, and as a result of its binding to the receptor, it can inhibit the binding of the receptor to the substances that can induce production of granulocyte colony-stimulating factor, but it in itself blocks production of granulocyte colony-stimulating factor, which are obtained by the method described above. The invention still further provides a substance which can bind to the receptor, and (a) as a result of its binding to the receptor, it can induce a change in the receptor, transmit signals into the cell via the receptor, and induce production of granulocyte colony-stimulating factor; (b) as a result of its binding to the receptor, it can inhibit the binding of the receptor to the substances that can induce production of granulocyte colony-stimulating factor, but it in itself does not induce production of granulocyte colony-stimulating factor; or (c) as a result of its binding to the receptor, it can inhibit the binding of the receptor to the substances that can induce production of granulocyte colony-stimulating factor, but it in itself inhibits production of granulocyte colony-stimulating factor. Such substances will hereinafter be referred to as "substances of the invention".

Examples of substances of the invention include the antibody of the invention, its fragments and other low molecular compounds, among which there are those with the effect of inducing production of granulocyte colony-stimulating factor, those with the effect of inhibition of receptor binding to the substances that can induce production of granulocyte colony-stimulating factor, and those with the effect of inhibition of receptor binding to the substances that can induce production of granulocyte colony-stimulating factor, while those also inhibit production of granulocyte colony-stimulating factor.

When the substance of interest is an antibody, the binding to the receptor (or binding inhibition) can be measured by a method, such as, for example, analysis of the antibody-bound macrophage cells using flow cytometry or ELISA.

Inducing effect (or inhibiting effect) of the production of granulocyte colony-stimulating factor can be determined by the method described in Japanese Unexamined Patent Publication HEI No. 11-106400. The outline of the process is given below.

The G-CSF promoter gene is inserted between the XhoI and the NcoI site of PicaGene Enhancer Vector 2 (product of Wako Junyaku Kogyo Co., Ltd.), in order to construct vector Pica G-CSF neo, the luciferase gene is linked downstream therefrom in place of the G-CSF gene itself, and then a neomycin resistance gene cut out from pMC1Neo PolyA at the SalI site downstream from SV40 also. This vector is introduced into the RAW264.7 cells by electroporation. The obtained cells are treated with medium containing geneticin, and the colony-forming cells are selected. Among the geneticin-resistant clones, clones exhibiting luciferase activity upon induction are further selected. Northern blot analysis using $^{32}$P-labeled mouse G-CSF cDNA as the probe is made to confirm that the luciferase activity reflects actual expression of the G-CSF mRNA. The transformed macrophage cells obtained in this manner are plated in a 96-well microtiter plate at $5 \times 10^4$ cells per well and cultured at 37° C. for 24 hours, and then after treating them with a prepared agonist or antagonist, as need, or the substance of interest is added at concentrations of about 0, 3.75, 7.5, 15, 30 and/or 60 μg/ml. After further culturing at 37° C. for 18 hours, the luciferase activity is measured.

(Use of Gene of the Invention as Drug Agent)

The gene of the invention may be utilized, for example, for diagnosis, prevention and therapy (gene therapy, etc.) of diseases in which neutrophils, a type of blood leukocyte, are involved (such as neutropenia). The protein, a part of the protein or the peptides thereof, antibody or its fragment, receptor, or the substance of the invention (hereinafter these will sometimes be referred to collectively as "protein, etc. of the invention") can serve as a drug to regulate the number of neutrophils in the blood or bone marrow. That is, the gene and protein, etc. of the invention can be used for treatment of neutropenia as a side effect of anticancer agents or neutropenia directly following bone marrow transplantation, and for diagnosis, prevention and treatment of anaplastic anemia.

The protein, etc. of the invention may generally be administered systemically or locally, usually in a parenteral form. Intravenous administration is particularly preferred for the parenteral forms.

The gene of the invention may be administered systemically or locally in the form of "gene therapy", wherein the gene is introduced into cells either in vivo or ex vivo. Introduction of the gene can be accomplished, for example, by the method described in Biomanual UP Series, Idenshi Chiryo no Kiso Gijutsu [Fundamental Techniques for Gene Therapy], Shimada, T., Saito, I., Ozawa, T., ed.: Yodosha Publishing, 1996. For introduction into cells ex vivo, there may be methods employing a retrovirus vector, adenovirus vector, adeno-associated virus (AAV) vector, cationic liposomes, HVJ-liposomes, or the calcium phosphate method, DEAE dextran method, etc. For introduction into cells in vivo, there may be methods employing a retrovirus vector, adenovirus vector, adeno-associated virus (AAV) vector, cationic liposomes or HVJ-liposomes.

The administration dosage will differ depending on age, gender, body weight, symptoms, treatment effect, administration route, treatment time and substance administrated (types of the protein or gene). But parenteral administration one to several times per day may be given at a dosage in the range of 1 µg to 100 g and preferably in the range of 10 µg to 1000 mg for each time for adults. Since the administration dosage will vary depending on the conditions, a dosage below this range will often be sufficient, or a dosage exceeding this range may be necessary. Injections for parenteral administration according to the invention include sterile aqueous or nonaqueous solutions, suspensions and emulsions. For aqueous and nonaqueous solutions and suspensions, one or more active substances are mixed with at least one inactive diluting agent. As examples of aqueous diluting agents, there may be distilled water for injection and physiological saline. As examples of nonaqueous diluting agents, there may be propylene glycol, polyethylene glycol, vegetable oils, such as olive oil, and alcohols, such as ethanol.

Such a composition may also include adjuvants, such as preservatives, humectants, emulsifiers, dispersers and stabilizers (for example, arginine and aspartic acid).

These can be sterilized by passage through a bacteria capturing filter, mixture with a sterilizer or irradiation. They may also be prepared as sterile solid compositions by lyophilization, for example, and then dissolved in sterile distilled water for injection or another solvent prior to use.

Other compositions for parenteral administration include external applications or suppositories and pessaries for enteric administration, which are formulated according to ordinary methods and contain one or more active substances.

The invention will now be explained in greater detail by way of the following examples, with understanding that the invention is in no way restricted by these examples.

EXAMPLES

Example 1

Cloning of Antigen Gene Recognized by the Monoclonal Antibody from Macrophage Cell Line (1) Preparation of poly(A)$^+$ RNA from Macrophage Cells (RAW264.7)

Guanidium thiocyanate-phenol-chloroform single-step extraction (Laboratory Manuals of Genetic Engineering, 3rd Edition, pp. 83-84, 1996) was used to prepare approximately 0.3 mg of total mRNA from $2 \times 10^8$ mouse macrophage cells (RAW264.7). This was purified using an oligo(dT) cellulose column to obtain 5 µg of poly(A)$^+$ RNA.

(2) Synthesis of Double-Stranded cDNA from Poly(A)$^+$ RNA

A reaction solution (50 µl) containing the poly(A)$^+$ RNA as obtained above (1) (5 µg), a reverse transcriptase (MMLV-RTase; product of STRATAGENE Corp.; 70 units) and dNTPs (0.6 mM) was incubated at 37° C. for 60 minutes to synthesize of a first strand cDNA. Next, a reaction solution containing the aforementioned reaction solution (45 µl), DNA polymerase (product of STRATAGENE Corp.; 100 units) and dNTPs (0.3 mM) was incubated at 16° C. for 150 minutes to synthesize a second strand cDNA, to obtain double-stranded cDNA (8 µg).

(3) Construction of cDNA Library

The method of Gubler-Hoffmann (Gubler, U. and Hoffmann, B. J.: Gene, 25:263-269, 1983) was used PfuDNA polymerase was used to blunt the ends of the double-stranded cDNA as synthesized above (2), and an adapter was linked thereto, by ligation with T4DNA ligase. Specifically, a reaction solution (total: 225 µl) containing the double-stranded cDNA as obtained above (2) (8 µg DNA; 200 µl) and PfuDNA polymerase (5 units) was incubated at 72° C. for 30 minutes.

The adapter-linked DNA was cleaved at the ends with restriction enzyme XhoI, and the cDNA longer than 0.5 kbp was fractionated with a gel column. This cDNA was incorporated into λZAPII phage vector (STRATAGENE Corp.) with T4DNA ligase following common protocol, and then by ligation into phage particles. Measurement of the phage titer showed that the cDNA library contained $2 \times 10^6$ independent clones. The obtained phage library was used to infect E. coli (XL1-Blue MRF') and was allowed to proliferate to $3.4 \times 10^9$ pfu/ml.

(4) Screening of Genes Encoding Protein that Bind to Antibodies that Show the Ability to Induce Granulocyte Colony-Stimulating Factor The cDNA library as constructed above (3) was subjected to immunoscreening using monoclonal antibodies (produced by the hybridoma deposited as FERM BP-6103; described in Japanese Patent Application HEI No. 9-266591), which shows the ability to induce granulocyte colony-stimulating factor (G-CSF) as the prove. The specific procedure was as follows.

E. coli (XL1-BlueMRF') infected with the phage cDNA library was seeded onto a 150 mm diameter plate. The plate was incubated at 42° C. for 4 hours that allowed the formation of the plaques of approximately 0.5 mm diameter. Then, microcellulose membranes, which were immersed in 10 mM of IPTG (isopropylthio-p-galactoside) and air-dried, were placed on those plates and incubated for 3 hours at 37° C. The nitrocellulose membrane was peeled off, and incubated in TBS-T (20 mM Tris-HCl, pH 7.6, 0.1% Tween20) containing 5% skim milk for one hour for blocking the membranes, while agitating at room temperature. This was followed by rinsing of the membrane gently for 2 minutes with TBS-T (repeated twice), immersing in a buffer at room temperature for 15 minutes (once) and washing for 5 minutes (twice). The nitrocellulose membrane was incubated for one hour at room temperature for reaction with the antibodies while agitating in the diluted primary antibody solution (produced by the hybridoma deposited as FERM BP-6103; 1.6 µg/ml). The nitrocellulose membrane was then washed in the same manner as the previous washing. Alkaline phosphatase-labeled secondary antibodies (ZYMED) were diluted to 0.6 µg/ml with TBS containing 1% BSA, and the nitrocellulose membrane was incubated for one hour at room temperature for reaction with the antibodies, while agitating in the diluted secondary antibody solution. The nitrocellulose membrane was again thoroughly washed in the same manner as described above, and finally washed with TBS for 5 minutes. After adding 1 ml of each NBT solution (50 mg/ml of NitroBlue Tetrazolium in 70% dimethylformamide) and BCIP solution (50 mg/ml of 5-bromo-4-chloro-3-indolyl phosphate in dimethylformamide) to a buffer solution containing 100 mM of Tris-HCl (pH 9.5), 100 mM of NaCl and 5 mM of $MgCl_2$, the nitrocellulose membrane was immersed therein. Reaction was carried out for 30 minutes in a dark room, and the membrane was washed with water and dried. After drying, the plaques exhibiting positive reaction on the nitrocellulose membrane were collected from the original plate.

Finally, 22 antibody-binding positive clones were obtained from $7 \times 10^5$ phage in the first screening. The top agarose containing the positive plaques were collected, and amplified. The second, third and fourth screenings were performed from approximately 1000 phages following the same procedure described above, resulting in isolation of 3 positive clones (MMR10, MMR17 and MMR19).

(5) Determination of the Nucleotide Sequence of the Gene

The inserts of the 3 positive clones (MMR10, MMR17 and MMR19), as obtained above (4) were cut out from the λXZAPII phage vectors by in vivo excision following a common procedure, and subcloned by converting the vector to pBluescript SK(-) Phagemid. The subcloned plasmids were made large quantity in E. Coli (SOLR), and approximately 20 µg of the plasmid DNA was obtained. The Primer Walking method was used to analyze the nucleotide sequences of these DNA.

Based on the results of the nucleotide sequence analyses, a clone MMR19 was found to have the 840 bp nucleotide sequence of the full length cDNA which included the open reading frame of the protein. The nucleotide sequence of the clone MMR19 is listed as SEQ ID NO:1 of the Sequence Listing.

(6) Primary Structure of the Protein Deduced from the Nucleotide Sequence of cDNA Clone The primary structure of the protein (MMR-CAM) (listed as EQ ID NOS:1 & 2 in the Sequence Listing) deduced from the nucleotide sequence of the gene analyzed (5) consists of 241 amino acid residues, and the molecular weight as estimated from the amino acid sequence was approximately 27 kDa. MMR-CAM is thought to be a type I membrane glycoprotein with one membrane-spanning domain, which comprises an extracellular portion of 107 amino acids, a membrane-spanning portion of 23 amino acids and an intracellular portion of 111 amino acids. Homology search showed that no molecules were found similar to the protein of the invention in terms of the structure, suggesting that the protein of the invention does not belong to the existing family. Also, there is a portion with the extensive modifications by the type O sugar chains was present in the extracellular domain. Phosphorylation sites for protein kinase C, tyrosine kinase, etc. are present in the intracellular domain. These sugar chain binding sites and phosphorylation sites are believed to play on very important role in signal transduction.

Example 2

Expression of the Protein (MMR-CAM) of the Invention

The clone (MMR19) obtained in Example 1(4) was inserted into an expression vector (λZAPII) following a common procedure and transformed E. coli (XL1-Blue), then a transformant cell line was constructed. The transformed E. coli cells were cultured, and the culture supernatant was dot blotted and allowed to with the same monoclonal antibodies used as shown in (3), which was produced by hybridoma deposited as FERM BP-6103 as a probe. Following this process, it was confirmed that the culture supernatant contained the protein that bound to the monoclonal antibodies.

Example 3

Comparison of the Mouse-Derived Protein with other Homologous Proteins using Database Search A data-search was conducted for human genes homologous to the nucleotide sequence and amino acid sequence listed as SEQ ID NO:1 and determined in Example 1 on both the amino acid level and the DNA level databases using (DNA DATA BANK of JAPAN (DDBJ): Dept. of Education, National Institute of Genetics, Center for Information Biology). The results are shown in Tables 1 and 2. These results suggest that the gene of the invention is also conserved in humans with high homology.

TABLE 1

Homology on amino acid level

| Position within amino acid sequence of SEQ ID NO:1 | Matching in human homologue |
| --- | --- |
| 1 to 91 | 83/91 (91%) |
| 50 to 146 | 83/97 (85%) |
| 1 to 78 | 70/78 (89%) |
| 200 to 241 | 40/42 (95%) |
| 172 to 241 | 67/70 (95%) |
| 103 to 150 | 46/48 (95%) |
| 169 to 241 | 58/73 (79%) |

TABLE 2

Homology on DNA level

| Position within nucleotide sequence of SEQ ID NO:1 | Matching in human homologue |
| --- | --- |
| 519 to 736 | 189/218 (86%) |
| 666 to 689 | 23/24 (95%) |
| 381 to 403 | 22/23 (95%) |
| 709 to 727 | 19/19 (100%) |

Example 4

Cloning of the Human Homologue of the Antigen Gene

Guanidium thiocyanate-phenol-chloroform extraction was used to extract total RNA from human normal brain tissue, and the poly(A)+ RNA was purified using oligo(dT) cellulose. cDNA was synthesized from the Poly(A)+ RNA using reverse transcriptase (MMLV-RTase) and DNA polymerase. A sense primer of position 4 to 22 (CCATGTCTGGCTGTCAAGC (SEQ ID NO:5)) and an antisense primer of position 714 to 724 (CCATTTTCTCCAACTGGGAGC (SEQ ID NO:6)) of the mouse antigen gene (MMR19) sequence were prepared, and these primers and the human normal brain tissue cDNA as the template were used for PCR reaction. As a result, a partial cDNA of the human homologue of the mouse antigen gene (MMR19) was obtained. Next, the 3'RACE method and 5'TRACE method were carried out using a specific primer (GSP) for the human homologue partial cDNA and an adapter primer. An antisense primer (GTCAGAAGAGATTCAGGGTGACC (SEQ ID NO:7)) was prepared from the 3' RACE fragment and a sense primer (AAGCCGTG CGGAGATTGGAGG (SEQ ID NO:8)) from the 5' RACE fragment. As a result of LD-PCR, the full length cDNA of the human homologue including the open reading frame was obtained. The Primer Walking method was used to elucidate the 924 bp nucleotide sequence of the cDNA. The obtained nucleotide sequence is listed as [SEQ. ID. No.3] SEQ ID NO:3 of the Sequence Listing. The nucleotide sequence of the human homologue cDNA (924 bp) showed 84.8% homology (with 712 matching nucleotides out of 924) with the nucleotide sequence of the mouse antigen gene cDNA (840 bp).

The primary structure of the protein deduced from the nucleotide sequence of the obtained gene is listed as SEQ ID NOS:3 & 4, consisting of 242 amino acids. The deduced amino acid sequence showed 93.8% homology with the mouse form (with 226 matching residues out of 242). This protein is also thought to be a type I membrane glycoprotein with one membrane-spanning domain.

Effect of the Invention

The gene and the protein encoding by the gene (including fragments of the gene and fragments of the protein), antibody (including fragments thereof), receptor and substance of the invention are novel, and are useful for pharmaceutical purposes.

The gene and the protein encoding by the gene (including fragments of the gene and fragments of the protein), antibody (including fragments thereof) and receptor are also useful as analytical reagents for screening of substances (for example, monoclonal antibodies, proteins and other low molecular substances) that have the ability to induce granulocyte colony-stimulating factor.

Fragments of the gene of the invention are also useful as probes for screening of homologous genes derived from other organisms.

The invention claimed is:

1. An isolated gene encoding:
   (a) a protein having the amino acid sequence listed as SEQ ID NO:2 of the Sequence Listing; or
   (b) a protein having at least 95% identity with the amino acid sequence listed as SEQ ID NO:2 of the Sequence Listing through the conservative substitution of one or more amino acids and also binding to an antibody or an antibody fragment that is produced by the hybridoma cell line deposited as FERM BP-6103.

2. A gene according to claim 1, which is a mouse gene.

3. A recombinant vector containing a gene according to claim 1.

4. A transformed cell comprising a recombinant vector that contains the according to claim 1.

5. An isolated gene having:
   (a) the nucleotide sequence listed as SEQ ID NO:1 of the Sequence Listing;
   (b) a nucleotide sequence which encodes a protein having at least 95% identity with the amino acid sequence listed as SEQ ID NO:2 of the Sequence Listing through the conservative substitution of one or more amino acids and that can bind to an antibody or an antibody fragment this is produced by the hybridoma cell line deposited as FERM BP-6103; or
   (c) a nucleotide sequence which hybridizes with DNA having the nucleotide sequence listed as SEQ ID NO:1 of the Sequence Listing under stringent conditions of 6×SSC, 5×Denhardt's solution, 0.5% SDS, 25-68° C. or 0-50% formamide, 6×SSC, 0.5% SDS, 25-68° C. and which encodes a protein that can bind to an antibody or an antibody fragment that is produced by the hybridoma cell line deposited as FERM BP-6103.

6. Any of the following purified proteins:
   (a) a protein having the amino acid sequence listed as SEQ ID NO:2 of the Sequence Listing;
   (b) a protein having at least 95% identity with the amino acid sequence listed as SEQ ID NO:2 of the Sequence Listing through the conservative substitution of one or more amino acids and also binding to an antibody or an antibody fragment that is produced by the hybridoma cell line deposited as FERM BP-6103; or
   (c) a protein that is encoded by the DNA which hybridizes with DNA having the nucleotide sequence listed as SEQ ID NO:1 of the Sequence Listing under stringent conditions of 6×SSC, 5×Denhardt's solution, 0.5% SDS, 25-68° C. or 0-50% formamide, 6×SSC, 0.5% SDS, 25-68° C. and that binds to an antibody or an antibody fragment that is produced by the hybridoma cell line deposited as FERM BP-6103.

7. A purified protein according to claim 6, which is a mouse protein.

8. An isolated receptor for a substance that can induce production of granulocyte colony-stimulating factor, wherein the receptor comprises a protein according to claim 6 and is present in a cell which can produce granulocyte colony-stimulating factor.

9. A screening method for a substance, which can bind to the protein according to claim 6 or the receptor according to claim 8, which comprises:
   (i) providing a potential substance;
   (ii) exposing the potential substance to said protein or receptor; and
   (iii) testing for specific binding.

10. A composition comprising a gene according to claim 1, a protein according to claim 6, or a receptor according to claim 8.

11. The receptor of claim 8, wherein the cell which can produce granulocyte colony-stimulating factor is a macrophage.

12. An isolated receptor according to claim 8, wherein the substance that can induce production of granulocyte colony-stimulating factor is a monoclonal antibody or an antibody fragment.

13. An isolated receptor according to claim 8, wherein the substance that can induce production of granulocyte colony-stimulating factor is a monoclonal antibody that is produced by a hybridoma of the cell line deposited as FERM BP-6103 or an antibody fragment thereof.

14. An isolated gene which encodes a protein having at least 98% identity with the amino acid sequence listed as SEQ ID NO:2 of the Sequence Listing through the conservative substitution of one or more amino acids and also binding to an antibody or an antibody fragment that is produced by the hybridoma cell line deposited as FERM BP-6103.

* * * * *